(12) United States Patent
Hong et al.

(10) Patent No.: US 6,583,304 B2
(45) Date of Patent: Jun. 24, 2003

(54) METALLOCENE COMPOUNDS, METALLOCENE CATALYSTS INCLUDING THE COMPOUNDS AND METHODS OF POLYMERIZING OLEFINS WITH THE CATALYSTS

(75) Inventors: Sah Mun Hong, Teajeon (KR); Byoung Keel Sohn, Teajeon (KR); Sung Woo Kang, Taejeon (KR); Tae Soo Hwang, Teajeon (KR); Young Jae Jun, Teajeon (KR); Hyun Ki Youn, Teajeon (KR)

(73) Assignee: Daelim Industrial Co., Ltd., Seoul (KR)

( * ) Notice: Subject to any disclaimer, the term of this patent is extended or adjusted under 35 U.S.C. 154(b) by 98 days.

(21) Appl. No.: 09/784,212

(22) Filed: Feb. 16, 2001

(65) Prior Publication Data

US 2001/0025117 A1 Sep. 27, 2001

(30) Foreign Application Priority Data

Feb. 18, 2000 (KR) .......................... 2000-7809

(51) Int. Cl.$^7$ .......................... C07F 17/00; B01J 31/00; C08F 4/44
(52) U.S. Cl. ........................ 556/11; 556/12; 556/19; 556/20; 556/43; 556/53; 556/58; 526/127; 526/348.6; 526/351; 526/352; 526/943; 502/103; 502/117
(58) Field of Search ................. 556/11, 12, 19, 556/20, 43, 53, 58; 502/103, 117; 526/127, 348.6, 351, 352, 943

(56) References Cited

U.S. PATENT DOCUMENTS

| | | | |
|---|---|---|---|
| 4,874,880 A | 10/1989 | Miya et al. | 556/53 |
| 5,324,800 A | 6/1994 | Welborn, Jr. et al. | 526/160 |
| 5,780,659 A | 7/1998 | Schmid et al. | 556/11 |
| 6,087,290 A | * 7/2000 | Fottinger et al. | 502/103 |
| 6,329,312 B1 | * 12/2001 | Licht et al. | 502/117 |
| 6,355,819 B1 | * 3/2002 | Leino et al. | 556/11 |
| 6,369,253 B1 | * 4/2002 | Wilson Jr. et al. | 556/10 |

FOREIGN PATENT DOCUMENTS

| | | |
|---|---|---|
| DE | 26 08 933 | 9/1977 |
| DE | 30 07 725 | 9/1981 |
| DE | 43 12 270 | 10/1994 |
| EP | 0 129 368 | 12/1984 |

OTHER PUBLICATIONS

W. Kaminsky, M. Miri, H. Sinn and R. Woldt. *Makromol. Chem. Rapid Commun.*, Feb. 21, 1983. 417–421.
M.F. Lappert, C.J. Pickett, P.I. Riley and Paul I.W. Yarrow. "Metallocene Derivatives of Early Transition Metals." *J. Chem. Soc., Dalton Trans.* 1981. 805–813.
J.M. Manriquez, D.R. McAlister, E. Rosenberg, A.M. Shiller, K.L. Williamson, S.I. Chan and J.E. Bercaw. "Solution Structure and Dynamics of Binuclear Dinitrogen Complexes of Bis(pentamethylcyclopentadienyl)titanium(II) and Bis(pentamethylcyclopentadienyl)zirconium(II)." *J. Amer. Chem Soc.*, May 10, 1978. 3078–3083.
John A. Ewen. "Mechanisms of Stereochemical Control in Propylene Polymerizations with Soluble Group 4B Metallocene/Methylalumoxane Catalysts." *J. Am. Chem. Soc.*, 1984. 6355–6364.
J. Laane. "Synthesis of Silacyclobutane and Some Related Compounds." *J. Am. Chem. Soc.*, 1967. 1144–1147.
R. Damrauer, R.A. Davis, M.T. Burke, R.A. Karn and G.T. Goodman. "An Improved Cyclization Procedure for 3–Chloropropylchlorosilanes: Efficient Syntheses of Silacyclobutanes." *J. of Organometal. Chem.* 1972. 121–125.
H. Schnutenhaus and H.H. Brintzinger. "1,1–Trimethylenebis(η5–3–tert–butylcyclopentadienyl)–titanium(IV) Dichloride, a Chiral ansa–Titanocene Derivative." *Angew. Chem. In. Ed. Engl.* 1979. 777–778.
H. Köpf and W. Kahl. "Metallorganische Polychalkogenid–Chelate VII*. Iva–Elementverbruckte Metallocenophane." *J. of Organometal. Chem.* 1974. C37–C40.
J.A. Smith, J.V. Seyerl, G. Huttner and H. H. Brintzinger. "Molecular Structure and Proton Magnetic Resonance Spectra of Methylene and Ethylene–Bridged Dicyclopent Adienyltitanium Compounds." *J. of Organometal. Chem.* 1979. 175–185.
F.R.W.P. Wild, L. Zsolnai, G. Huttner and H.H. Brintzinger. "Synthesis and Molecular Structures of Chiral ansa–Titanocene Deivatives with Bridged Tetrahydroindenyl Ligands." *J. of Organometal. Chem.* 1982. 233–247.
H. Wesenfeldt, A. Reinmuth, E. Barsties, K. Evertz and H. H. Brintzinger. "Racemic and Meso Diastereomers of Group IV Metallocene Derivatives with Symmetrically Substituted, Dimethylsilanediyl;–Bridged Ligand Frameworks. Crystal Structure of R,S–Me2Si(3–t–Bu–5–MeC5H2)2ZrC12." 1989. 359–370.
T. Mise, S. Miya and H. Yamazaki. "Excellent Stereoregular Isotactic Polymerizations of Propylene with C2–Symmetric Silylene–Bridged Metallocene Catalysts." *Chem. Soc of Japan.* 1989. 1853–1856.

* cited by examiner

Primary Examiner—Porfirio Nazario-Gonzalez

(57) ABSTRACT

There are disclosed new metallocene compounds and catalysts for olefin polymerization. The metallocene compound is a complex of transition metal and cyclopentadienyl-type ligands substituted with silacycloalkyl group. The metallocene catalyst comprises the above metallocene compound and at least one activator such as aluminoxanes, aromatic boron compounds substituted with fluoride, and modified clays. The metallocene catalyst can be used for polymerization of olefin in liquid phase, slurry phase or gas phase process.

12 Claims, No Drawings

METALLOCENE COMPOUNDS, METALLOCENE CATALYSTS INCLUDING THE COMPOUNDS AND METHODS OF POLYMERIZING OLEFINS WITH THE CATALYSTS

BACKGROUND OF THE INVENTION (a). Field of the Invention

The present invention relates to metallocene compounds, metallocene catalysts including the compounds and methods of polymerizing olefins with the catalysts.

(b). Description of the Related Art

Catalysts including transition metals have been widely used for olefin polymerization. Lately, German Patent Nos. 2,608,933 and 3,007,725 have disclosed that metallocene compound consisting of Group 4B transition metal such as zirconium, titanium or hafnium, and ligand having cyclopentadienyl structure can be used as catalyst for olefin polymerization in the presence of an activator such as methylaluminoxane. The examples of the ligands having the cyclopentadienyl structures include cyclopentadiene, indene, fluorene, and substituted varieties of such compounds.

Various metallocene compounds having cyclopentadienyl-type ligands have been used to prepare the catalyst systems for the olefin polymerization. It has also been known that changes of chemical structures of the cyclopentadienyl ligands may produce significant effects on the suitabilities of metallocene compounds as the catalysts. For example, activities, stereospecificities, and stabilities of the catalysts, and physical properties of the polymers obtained by the polymerization depend on the sizes and positions of substituents bonded to cyclopentadienyl ligands.

In various documents such as European patent No. 129, 368, U.S. Pat. Nos. 4,874,880 and 5,324,800 and Makromol. Chem. Rapid Commun., 4, 417(1983) et al., it have also been disclosed that the catalyst systems including of metallocene compounds, which consists of substituted-cyclopentadienyl ligands and zirconium as the transition metal, and methylaluminoxane have high activities in the olefin polymerization. In addition, the metallocene compounds consisting of zirconium and cyclopentadienyl ligands substituted with hydrocarbyl group are also known. For examples, bis(alkylcyclopentadienyl) zirconium dichloride (wherein, alkyl represents methyl, ethyl, isopropyl, tert-butyl or trimethylsilyl.) [J. Chem. Soc. Dalton Trans., 805(1981)], bis(pentamethylcyclopentadienyl)zirconium dichloride [J. Amer. Chem. Soc., 100, 3078(1978)], (pentamethylcyclopentadienyl) (cyclopentadienyl) zirconium dichloride [J. Amer. Chem. Soc., 106, 6355 (1984)], bis(di, tri, or tetra alkyl-cyclopentadienyl) zirconium dichloride [U.S. Pat. No. 4,874,880], non-bridged metallocene compounds having substituted indenyl ligands [U.S. Pat. No. 5,780,659], metallocene compounds having mono substituted cyclopentadienyl ligand [German patent No. 4,312,270] are known.

Even though the activities of the metallocene catalysts have been progressively increased by changing the structures of the metallocene compounds, there exists a need for the better metallocene catalysts having sufficient activities to prepare polyolefin of high molecular weight and better physical properties.

SUMMARY OF THE INVENTION

Thus, the present invention is directed to the preparation of polyolefin with novel catalyst systems, which include metallocene compounds consisting of cyclopentadienyl-type ligands having silacycloalkyl substituents and transition metal such as zirconium, titanium or hafnium.

It is, therefore, an object of the present invention to provide novel metallocene compounds, which forms metallocene catalysts for olefin polymerization.

It is another object of the present invention to provide new metallocene catalysts prepared from the metallocene compounds.

It is also another object of the present invention to provide methods of polymerizing olefins with the metallocene catalysts.

In accordance with an embodiment of the present invention, there is provided metallocene compounds of the following formula 1 or 2, which can be used to prepare metallocene catalysts for olefin polymerization.

$$(CpR^1_a R^s_b)(Cp'R^2_{a'} R^s_{b'})MX_2 \quad \text{[Formula 1]}$$

[Formula 2]

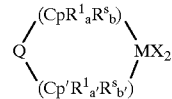

In formula 1 and 2, Cp and Cp', which can be the same or different, represent a radical selected from the group consisting of cyclopentadienyl radical, indenyl radical, 4,5,6,7-tetrahydro-1-indenyl radical and fluorenyl radical;

$R^1$ and $R^2$, which can be the same or different, represent phosphine, amino, alkyl having 1 to 20 carbon atoms, alkoxy, alkylamino, dialkylamino, alkoxy-alkyl, aryl, aryloxy-alkyl, alkenyl, alkylaryl or arylalkyl radical;

$R^s$ represents 1-alkyl-1-silacyclohydrocarbyl radical of the following formula 3,

[Formula 3]

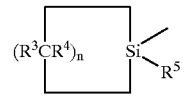

wherein, $R^3$ and $R^4$, which can be the same or different, represent hydrogen or alkyl radical having 1 to 5 carbon atoms, $R^5$ is alkyl radical having 1 to 8 carbon atoms, and n is an integer of 4 to 8;

$Cp'R^2_{a'}$, $R^s_{b'}$ in the formula 2 can be displaced with divalent NR'' radical, wherein R'' represents $R^s$, alkyl radical having 1 to 12 carbon atoms, or aryl radical having 6 to 10 carbon atoms;

M represents a Group 4B, 5B, 6B transition metal, and preferably represents titanium, zirconium or hafnium;

X, which can be the same or different, represents one radical selected from the group consisting of halogen, alkyl radical having 1 to 20 carbon atoms, aryl, alkenyl, alkylaryl, arylalkyl, alkoxy and aryloxy radicals; and Q represents alkylene radical having 1 to 4 carbon atoms, dialkyl germanium or silicon, alkyl phosphine or amine radical, bis-dialkylsilyl or bis-dialkylgermanyl having hydrocarbyl radical of 1 to 4 carbon atoms.

In formula 1, a is an integer of 0 to 4, a' is an integer of 0 to 5, b is an integer of 1 to 3, and b' is an integer of 0 to 3, wherein $1 \leq a+b \leq 5$, $0 \leq a'+b' \leq 5$; and in formula 2, a is an integer of 0 to 3, a' is an integer of 0 to 4, b is an integer of 1 to 2, and b' is an integer of 0 to 3, wherein $1 \leq a+b \leq 4$, $0 \leq a'+b' \leq 4$.

In accordance with another embodiment of the present invention, there is provided metallocene catalysts comprising:

at least one metallocene compound selected from the compounds represented by formula 1 or 2; and at least one activator selected from the group consisting of aluminoxanes represented by the following formula 4 or 5, aromatic boron compounds substituted with fluoride, and modified clays.

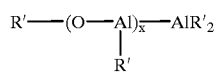

[Formula 4]

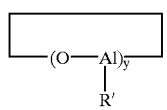

[Formula 5]

In the formula 4 and 5, R', which can be the same or different, represent hydrocarbyl radical having 1 to 10 carbon atoms, x is an integer of 1 to 50, and y is an integer of 3 to 50.

In accordance with another embodiment of the present invention, there is provided methods of polymerizing olefins with the metallocene catalysts comprising:

at least one metallocene compound selected from the compounds represented by formula 1 or 2; and at least one activator selected from the group consisting of aluminoxanes represented by the following formula 4 or 5, aromatic boron compounds substituted with fluoride, and modified clays.

The methods of polymerizing olefins preferably include liquid phase polymerization, slurry phase polymerization or gas phase polymerization.

DETAILED DESCRIPTION OF THE PREFERRED EMBODIMENTS

The present invention will be illustrated in detail by the following preferred embodiments.

The present invention is to provide methods of polymerizing olefins in the presence of the metallocene catalysts comprising at least one metallocene compounds of the formula 1 or 2, which consist of cyclopentadienyl-type ligands substituted with silacycloalkyl radical and a Group 4B, 5B, 6B transition metal. Hereinafter, the method for preparing the metallocene compounds of the present invention will be described step by step in detail, and then the preferable examples of metallocene compounds of the present invention will be provided.

The metallocene compounds, $(CpR^1_a R^s_b)_2 MX_2$, which is a compound of formula 1 when $CpR^1_a R^s_b$ is the same with $Cp'R^2_{a'} R^s_{b'}$, can be prepared by the following 7 steps.

Step 1 is to produce a compound represented by $R^s X'$ by reacting $X'(CR^3 R^4)_n Si(R^5) X'_2$ with magnesium according to the well known cyclization reaction shown in the following reaction scheme 1.

[Reaction scheme 1]

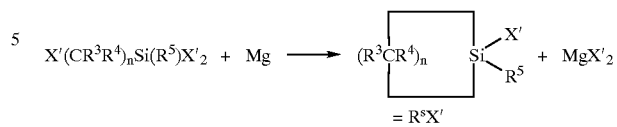

$= R^s X'$

In reaction scheme 1, $R^s$ represents 1-alkyl-1-silacyclohydrocarbyl radical of the above formula 3, $R^3$ and $R^4$, which can be the same or different, represent hydrogen or alkyl radical having 1 to 5 carbon atoms, $R^5$ is alkyl radical having 1 to 8 carbon atoms, n is an integer of 4 to 8, and X' is Cl, Br or I.

The following reaction scheme 2 is a example for preparing the compound of $R^s X'$ according to the step 1, and is disclosed in J. Amer. Chem. Soc., 89,1144(1967) and J. Organometal. Chem., 43,121(1972).

[Reaction scheme 2]

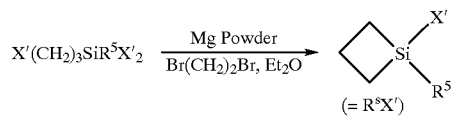

$(= R^s X')$

In reaction scheme 2, X', $R^5$ and $R^s$ represent same radicals defined in the reaction scheme 1.

The reaction may be performed in the presence of the solvent of diethyl ether at a temperature of 0 to 60° C. for 1 to 15 days. To separate the compound of $R^s X'$ from the reaction product, which is a mixture of liquid and solid phase, the liquid phase is filtered and fractional-distilled to obtain the compound of $R^s X'$, or the product can be directly fractional-distilled to obtain the compound of $R^s X'$. Since the 1-alkyl-1-silacyclohydrocarbyl halide($R^s X'$) has so high boiling point that it is difficult to separate it and its yield is very low, the separating process should be very precisely controlled.

Accordingly, to obtain the compound of $R^s X'$ with high yield, two or more traps can be connected with the reactor to separate the liquid phase from the solid material under vacuum, and then pure 1-alkyl-1-silacyclohydrocarbyl halide ($R^s X'$) can be obtained by slow fractional-distillation of the liquid phase.

In step 2, $M'(CpR^1_a)$ or $Li(CpR^1_a)$ is obtained by reacting the compound $CpR^1_a$ with alkali metal M' (for example, sodium or potassium) or metallating agent such as alkyl lithium (for example, butyl lithium), and the obtained M' $(CpR^1_a)$ or $Li(CpR^1_a)$ reacts with the compound $R^s X'$ to produce $CpR^1_a R^s$ as shown in the following reaction scheme 3.

[Reaction scheme 3]

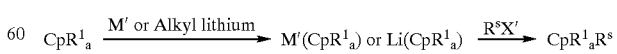

In reaction scheme 3, Cp represents a radical selected from the group consisting of cyclopentadienyl radical, indenyl radical, 4,5,6,7-tetrahydro-1-indenyl radical and fluorenyl radical. $R^1_a$, which are substituted to Cp and can be the same or different, represent phosphine, amino, alkyl having 1 to 20 carbon atoms (for example, methyl, ethyl, propyl, isopropyl, butyl, sec-butyl, tert-butyl, pentyl and the like), alkoxy, alkylamino, dialkylamino, alkoxy-alkyl, aryl, aryloxy-alkyl, alkenyl, alkylaryl or arylalkyl radical, and preferably is alkyl radical having 1 to 6 carbon atoms. "a" is an integer of 0 to 4, and $R^s$ and $X'$ represent same radicals defined in the reaction scheme 1.

The compound $CpR^1_a$ can be prepared according to any conventional method. The compound $CpR^1_a$ is converted into the corresponding metal compound $Na(CpR^1_a)$, $K(CpR^1_a)$ or $Li(CpR^1_a)$ by the reaction with a metallating agent such as Na, K or alkyl lithium. The conversion into such metal compound may be generally performed under inert gas atmosphere such as nitrogen and in the presence of solvent at −78 to 60° C. for 2 to 40 hours. The solvent used in the process may include diethyl ether, diethyleneglycol diethylether, letrahydrofuran (THF), pentane, hexane, heptane and the like. More preferable solvent includes diethyl ether, tetrahydrofuran (THF), pentane or hexane. The obtained organometallic compound may be directly used in the next reaction step, or may be separated and kept in the form of solid powder for the use in the next step.

The reaction of the organometallic compound $Na(CpR^1_a)$, $K(CpR^1_a)$ or $Li(CPR^1_a)$ with the compound $(R^s X')$ can be carried out in the presence of the solvent such as diethyl ether, tetrahydrofuran (THF), pentane, hexane or the like at a temperature of −78 to 70° C. for 2 to 28 hours. After the reaction is complete, the next reaction step can be directly performed in the same reactor, or the precipitate of metal salt can be removed by filtration or centrifugation, and the ligand compound of $(CpR^1_a R^s)$ having the cyclopentadienyl structure can be obtained through purification.

Step 3 is to prepare the compound $Li(CpR^1_a R^s)$ by reacting $CpR^1_a R^s$ produced in step 2 with metallating agent such as alkyl lithium (for example, butyl lithium) as shown in the following reaction scheme 4.

[Reaction scheme 4]

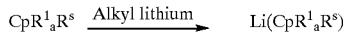

The reaction step 3 may be performed in the presence of solvent at a temperature of −78 to 60° C. for 2 to 40 hours. The solvent for the reaction may include diethyl ether, diethyleneglycol diethylether, tetrahydrofuran (THF), pentane, hexane, heptane, or the like. More preferable examples of the solvents include diethyl ether, tetrahydrofuran (THF), pentane or hexane. The resultant organometallic compound may be directly used in the next reaction, or may be separated and kept in the form of solid powder for the use in the next step.

Step 4 is to prepare the compound $(CpR^1_a R^s)_2 MX_2$ by reacting $Li(CpR^1_a R^s)$ produced in the step 3 with $MX_4$ as shown in the following reaction scheme 5.

[Reaction scheme 5]

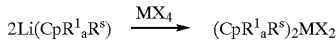

In step 4, the organometallic compound $Li(CpR^1_a R^s)$ is mixed and reacted with the transition metal halide $MX_4$ in the presence of solvent, wherein M represents a Group 4B, 5B, 6B transition metal, and X represents halogen. The more preferable transition metal M includes titanium, zirconium or hafnium, and more preferable halogen X includes Cl, Br or I. The reaction may be performed in the presence of solvent at a temperature of −78 to 60° C. for 1 hour to 3 days. The suitable solvent for reaction step 4 includes diethyl ether, diethyleneglycol diethylether, tetrahydrofuran (THF), dichloromethane, and the like. The obtained product $(CpR^1_a R^s)_2 MX_2$ can be purified through evaporation of the solvent, filtration, and recrystallization or sublimation.

The compound $Li(CpR^1_a R^s_b)$ can be prepared by repeating steps 2 and 3, and $(CpR^1_a R^s_b)_2 MX_2$ can be prepared by carrying out the step 4 with the compound $Li(CpR^1_a R^s_b)$. When $CpR^1_a R^s_b$ is different from $Cp'R^2_a R^s_{b'}$ in the metallocene compounds of the formula 1, $Li(CpR^1_a R^s_b)$ is reacted with $(Cp'R^2_a R^s_{b'})M_3$ to obtain $(CpRhu 1_a R^s_b)(Cp'R^2_a R^s_{b'})MX_2$. Namely, to prepare the asymmetric metallocene compounds of the formula 1 in which $CpR^1_a R^{sb}$ is different from $Cp'R^2_a R^s_{b'}$, $Li(CpR^1_a R^s_b)$ and $(Cp'R^2_a R^s_{b'})MX_3$ are dissolved into solvent with same equivalent and mixed for reaction. Cp' and $R^2$ have same meanings with Cp and $R^1$, and can be same or different with Cp and $R^1$, respectively, and a' is an integer of 0 to 5. b is an integer of 1 to 3, and b' is an integer of 0 to 3, wherein $1 \leq a+b \leq 5$, $0 \leq a'+b' \leq 5$.

This reaction may be performed in the presence of solvent at a temperature of −78 to 60° C. for 1 hour to 3 days. The solvent used in the reaction may include diethyl ether, diethyleneglycol diethyl ether, tetrahydrofuran (THF), dichloromethane. The product produced by the reaction can be purified through evaporation of the solvent, filtration, and recrystallization or sublimation.

The method of preparing the metallocene compounds of the formula 2 in the case of $CpR^1_a R^s_{b'}$ being same with $Cp'R^2_a R^s_b$ will be described in detail, below. The metallocene compounds of the formula 2 can be prepared through the same steps 1, 2 and 3 as in the preparation of the metallocene compounds of the formula 1, and further through steps 5 to 7, which will be described below.

Step 5 is to react the product of the step 3 with one or more compounds represented by $X^1 Q X^2$ as shown in the following reaction scheme 6.

[Reaction scheme 6]

In reaction scheme 6, $X^1$ and $X^2$, which can be the same or different, represent Cl, Br, I or —$OSO_2 R^6$ (example: -O-tosyl radical), and $R^6$ represents alkyl radical having 1 to 6 carbon atoms or aryl radical having 6 to 10 carbon atoms.

In this reaction, the organometallic compound $Li(CpR^1_a R^s)$ produced in the step 3 is reacted with one or more bridging agents $X^1 Q X^2$ according to the reaction scheme 6 to obtain a bridged compound, in which the two cyclopentadienyl compounds $CpR^1_a R_S$ are cross-linked with each other through the functional group Q, which represents alkylene radical having 1 to 4 carbon atoms, dialkyl germanium or silicon, alkyl phosphine or amine radical, bis-dialkylsilyl or bis-dialkylgermanyl having hydrocarbyl radical of 1 to 4 carbon atoms. Typical examples of the compound $X^1 Q X^2$ may include 1,2-dibromoethane ($BrCH_2 CH_2 Br$) and dichlorodimethylsilane ($Me_2 SiCl_2$) [Angew. Chem., Int. Ed. Engl. 777, 18(1979); J. Organometal. Chem., 64, C37(1974); J. Organometal. Chem., 173, 175(1979); J. Organometal. Chem., 232, 233(1982); J. Organometal. Chem., 369, 359(1989); Chem. Lett., 1853(1989)].

This reaction may be performed in the presence of solvent at a temperature of −78 to 70° C. for 2 to 48 hours. After completion of this reaction, the obtained compound can be directly used in the next reaction, or the precipitate of metal salt can be removed by filtration or centrifugation, and the bridged ligand compound $(CpR^1_aR^s)_2Q$ can be obtained through purification. The solvent used in the reaction may include diethyl ether, tetrahydrofuran (THF), and dichloromethane.

Step 6 is to react the product of the step 5 with metallating agent such as alkyl lithium to obtain the compound $Li_2(CpR^1_aR^s)_2Q$ as shown in the reaction scheme 7.

[Reaction scheme 7]

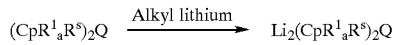

The step 7 for preparing the metallocene compound of the formula 2, is to react the compound of $Li_2(CpR^1_aR^s)_2Q$ produced by the step 6 with transition metal halide $MX_4$ to obtain the compound of $Q(CpR^1_aR^s)_2MX_2$ as shown in the reaction scheme 8.

[Reaction scheme 8]

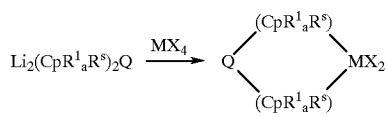

This reaction may be performed in the presence of solvent at a temperature of −78 to 70° C. for 4 to 48 hours. After completion of this reaction, the product of $Q(CpR^1_aR^s)_2MX_2$ can be purified through evaporation of the solvent, filtration, and recrystallization or sublimation. The suitable solvent includes diethyl ether, tetrahydrofuran (THF), and dichloromethane.

The compound represented by $Li(CpR^1_aR^s_b)$ can be prepared by repeating steps 2 and 3, and $Q(CpR^1_aR^s_b)MX_2$ can be prepared by carrying out the step 5, 6 and 7 with the compound $Li(CpR^1_aR^s_b)$. When $CpR^1_aR^s_b$ is lo different from $Cp'R^2_{a'}R^s_{b'}$ in the metallocene compounds of the formula 2, the steps 6 and 7 are performed using $(CpR^1_aR^s_b)Q(Cp'R^2_{a'}R^s_{b'})$ instead of $Q(CPR^1_aR^s_b)_2$. In this case, a is an integer of 0 to 3, a' is an integer of 0 to 4, b is an integer of 1 to 2, and b' is an integer of 0 to 3, wherein $1 \leq a+b \leq 4$, $0 \leq a'+b' \leq 4$.

The typical and non-limiting examples of the metallocene compounds of the formula 1 or 2, in the case where the transition metal is zirconium, include bis((1-methyl-1-silacyclobutyl)-cyclopentadienyl)zirconium dichloride, bis((1-ethyl-1-silacyclobutyl)-cyclopentadienyl)zirconium dichloride, bis((1-propyl-1-silacyclobutyl)-cyclopentadienyl)zirconium dichloride, bis((1-butyl-1-silacyclobutyl)-cyclopentadienyl)zirconium dichloride, bis(1-methyl-3-(1-methyl-1-silacyclobutyl)-cyclopentadienyl)zirconium dichloride, bis(1-methyl-3-(1-ethyl-1-silacyclobutyl)-cyclopentadienyl)zirconium dichloride, bis(1-methyl-3-(1-propyl-1-silacyclobutyl)-cyclopentadienyl)zirconium dichloride, bis(1-methyl-3-(1-butyl-1-silacyclobutyl)-cyclopentadienyl)zirconium dichloride, bis(1-ethyl-3-(1-methyl-1-silacyclobutyl)-cyclopentadienyl)zirconium dichloride, bis(1-ethyl-3-(1-ethyl-1-silacyclobutyl)-cyclopentadienyl)zirconium dichloride, bis(1-ethyl-3-(1-propyl-1-silacyclobutyl)-cyclopentadienyl)zirconium dichloride, bis(1-(1-butyl-1-silacyclobutyl)-3-ethyl-cyclopentadienyl)zirconium dichloride, bis(1-butyl-3-(1-methyl-1-silacyclobutyl)-cyclopentadienyl)zirconium dichloride, bis(1-butyl-3-(1-ethyl-1-silacyclobutyl)-cyclopentadienyl)zirconium dichloride, bis(1-butyl-3-(1-propyl-1-silacyclobutl)-cyclopentadienyl)zirconium dichloride, bis(1-butyl-3-(1-butyl-1-silacyclobutyl)-cyclopentadienyl)zirconium dichloride, bis(1-(1-methyl-1-silacyclobutyl) indenyl) zirconium dichloride, bis(1-(1-ethyl-1-silacyclobutyl)indenyl)zirconium dichloride, bis(1-(1-propyl-1-silacyclobutyl)-indenyl)zirconium dichloride, bis(1-(1-butyl-1-silacycl obutyl)indenyl)zirconium dichloride, bis(1-(1-methyl-1-silacyclobutyl)tetrahydroindenyl)zirconium dichloride, bis(1-(1-ethyl-1-silacyclobutyl)tetrahydroindenyl)zirconium dichloride, bis(1-(1-propyl-1-silacyclobutyl)tetrahydroindenyl)zirconium dichloride, bis(1-(1-butyl-1-silacyclobutyl)tetrahydroindenyl)zirconium dichloride, bis(9-(1-methyl-1-silacyclobutyl)fluorenyl)zirconium dichloride, bis(9-(1-ethyl-1-silacyclobutyl)fluorenyl)zirconium dichloride, bis(9-(1-propyl-1-silacyclobutyl)fluorenyl)zirconium dichl oride, bis(9-(1-butyl-1-silacyclobutyl)fluorenyl)zirconium dichloride, (1-(1-methyl-1-silacyclobutyl)indenyl)(cyclopentadienyl)zirconium dichloride, (1-(1-ethyl-1-silacyclobutyl)indenyl)(cyclopentadienyl)zirconium dichloride, (1-(1-propyl-1-silacyclobutyl)indenyl)(cyclopentadienyl)zirconium dichloride, (1-(1-butyl-1-silacyclobutyl)indenyl)(cyclopentadienyl)zirconium dichloride, (1-(1-methyl-1-silacyclobutyl)tetrahydroindenyl)(cyclopentadienyl)zirconium dichloride, (1-(1-ethyl-1-silacyclobutyl)tetrahydroindenyl)(cyclopentadienyl)zirconium dichloride, (1-(1-propyl-1-silacyclobutyl)tetrahydroindenyl)(cyclopentadienyl)zirconium dichloride, (1-(1-butyl-1-silacyclobutyl)tetrahydroindenyl)(cyclopentadienyl)zirconium dichloride, (1-(1-methyl-1-silacyclobutyl)indenyl)(pentamethylcyclopentadienyl)zirconium dichloride, (1-(1-ethyl-1-silacyclobutyl)indenyl)(pentamethylcyclopentadienyl)zirconium dichloride, (1-(1-propyl-1-silacyclobutyl)indenyl)(pentamethylcyclopentadienyl)zirconium dichloride, (1-(1-butyl-1-silacyclobutyl)indenyl)(pentamethyl-cyclopentadienyl)zirconium dichloride, (1-(1-methyl-1-silacyclobutyl)pentahydroindenyl) (pentamethylcyclopentadienyl)zirconium dichloride, (1-(1-ethyl-1-silacyclobutyl)pentahydroindenyl) (pentamethylcyclopentadienyl)zirconium dichloride, (1-(1-propyl-1-silacyclobutyl)pentahydroindenyl) (pentamethylcyclopentadienyl)zirconium dichloride, (1-(1-butyl-1-silacyclobutyl) pentahydroindenyl) (pentamethylcyclopentadienyl)zirconium dichloride, (1-(1-methyl-1-silacyclobutyl)cyclopentadienyl) (cyclopentadienyl)zirconium dichloride, (1-(1-ethyl-1-silacyclobutyl)cyclopentadienyl) (cyclopentadienyl)zirconium dichloride, (1-(1-propyl-1-silacyclobutyl)cyclopentadienyl) (cyclopentadienyl)zirconium dichloride, (1-(1-butyl-1-silacyclobutyl)cyclopentadienyl) (cyclopentadienyl)zirconium dichloride, (1-methyl-3-(1-methyl-1-silacyclobutyl)cyclo-pentadienyl)(cyclopentadienyl)zirconium dichloride, (1-(1-ethyl-1-silacyclobutyl)-3-methyl-cyclopentadienyl) (cyclopentadienyl)zirconium dichloride, (1-(1-propyl-1-silacyclobutyl)-3-methyl-cyclopentadienyl)(cyclopentadienyl)zirconium dichloride, (1-(1-butyl-1-silacyclobutyl)-3-methyl-cyclopentadienyl) (cyclopentadienyl)zirconium dichloride, ((1-methyl-1-silacyclobutyl)cyclopentadienyl) (pentamethylcyclopentadienyl)zirconium dichloride, ((1-ethyl-1-silacyclobutyl)cyclopentadienyl) (pentamethylcyclopentadienyl)zirconium dichloride, ((1-propyl-1-silacyclobutyl)cyclopentadienyl) (pentamethylcyclopentadienyl)zirconium dichloride, ((1-butyl-1-silacyclobutyl)cyclopentadienyl) (pentamethylcyclopentadienyl)zirconium dichloride, (1-methyl-3-(1-methyl-1-silacyclobutyl)cyclo-pentadienyl)(pentamethylcyclo pentadienyl)zirconium dichloride, (1-(1-ethyl-1-silacyclobutyl)-3-methyl-cyclopentadienyl) (pentamethylcyclo pentadienyl)zirconium dichloride, (1-methyl-3-(1-propyl-1-silacyclobutyl)cyclo-pentadienyl)(pentamethylcyclo pentadienyl) zirconium dichloride, (1-(1-butyl-1-silacyclobutyl)-3-methyl-cyclopentadienyl) (pentamethylcyclo pentadienyl) zirconium dichloride, bis(9-(1-methyl-1-silacyclobutyl)-fluorenyl) zirconium dichloride, bis(9-(1-ethyl-1-silacyclobutyl)-fluorenyl) zirconium dichloride, bis(9-(1-propyl-1-silacyclobutyl)-fluorenyl) zirconium dichioride, bis(9-(1-butyl-1-silacyclobutyl)-fluorenyl) zirconium dichloride, (9-(1-methyl-1-silacyclobutyl)-fluorenyl) (cyclopentadienyl) zirconium dichloride, (9-(1-ethyl-1-silacyclobutyl)-fluorenyl)(cyclopent-adienyl) zirconium dichloride, (9-(1-propyl-1-silacyclobutyl)-fluorenyl) (cyclopentadienyl) zirconium dichloride, (9-(1-butyl-1-silacyclobutyl)-fluorenyl)(cyclopent-adienyl) zirconium dichloride, (9-(1-methyl-1-silacyclobutyl)-fluorenyl) (pentamethylcyclopentadienyl) zirconium dichloride, (9-(1-ethyl-1-silacyclobutyl)-fluorenyl)(pentamethyl-cyclopentadienyl) zirconium dichloride, (9-(1-propyl-1-silacyclobutyl)-fluorenyl) (pentamethylcyclopentadienyl) zirconium dichloride, (9-(1-butyl-1-silacyclobutyl)-fluorenyl)(pentamethyl-cyclopentadienyl) zirconium dichloride, dimethylsilyl(1-(1-methyl-1-silacyclobutyl) cyclopentadienyl) (tert-butylamido) zirconium dichloride, dimethylsilyl(1-(1-methyl-1-silacyclobutyl) cyclopentadienyl) (sec-butylamido) zirconium dichloride, ethylene-bis(1-(1-methyl-1-silacyclobutyl)indenyl) zirconium dichloride, ethylene-bis(1-(1-ethyl-1-silacyclobutyl)indenyl) zirconium dichloride, ethylene-bis(1-(1-propyl-1-silacyclobutyl)indenyl) zirconium dichloride, ethylene-bis(1-(1-butyl-1-silacyclobutyl)indenyl) zirconium dichloride, ethylene-bis(1-(1-methyl-1-silacyclobutyl) tetrahydroindenyl)zirconium dichloride, ethylene-bis(1-(1-ethyl-1-silacyclobutyl) tetrahydroindenyl)zirconium dichloride, ethylene-bis(1-(1-propyl-1-silacyclobutyl) tetrahydroindenyl)zirconium dichloride, ethylene-bis(1-(1-butyl-1-silacyclobutyl) tetrahydroindenyl)zirconium dichloride, 2,2-propyl-bis(3-(1-methyl-1-silacyclobutyl)-1-indenyl) zirconium dichloride, 2,2-propyl-bis(3-(1-ethyl-1-silacyclobutyl)-1-indenyl) zirconium dichloride, 2,2-propyl-bis(3-(1-butyl-1-silacyclobutyl)-1-indenyl) zirconium dichloride, 2,2-propyl-bis(3-(1-methyl-1-silacyclobutyl)-1-tetrahydroindenyl)zirconium dichloride, 2,2-propyl-bis(3-(1-ethyl-1-silacyclobutyl)-1-tetrahydroindenyl)zirconium dichloride, 2,2-propyl-bis(3-(1-butyl-1-silacyclobutyl)-1-tetrahydroindenyl)zirconium dichloride, ethylene-bis(3-(1-methyl-1-silacyclobutyl) cyclopentadienyl) zirconium dichloride, 2,2-propyl-bis(3-(1-methyl-1-silacyclobutyl) cyclopentadienyl)zirconium dichloride, 2,2-propyl-(3-(1-methyl-1-silacyclobutyl) cyclopentadienyl)(cyclopentadienyl)zirconium dichloride, 2,2-propyl-(3-(1-methyl-1-silacyclobutyl) cyclopentadienyl)(pentamethyl cyclopentadienyl) zirconium dichloride.

The typical and non-limiting examples of the metallocene compounds of the formula 1 or 2, in the case where the transition metal is titanium, include bis((1-methyl-1-silacyclobutyl)-cyclopentadienyl) titanium dichloride, bis((1-ethyl-1-silacyclobutyl)-cyclopentadienyl)titanium dichloride, bis((1-propyl-1-silacyclobutyl)-cyclopentadienyl) titanium dichloride, bis((1-butyl-1-silacyclobutyl)-cyclopentadienyl)titanium dichloride, bis(1-methyl-3-(1-methyl-1-silacyclobutyl)-cyclopentadienyl)titanium dichioride, bis(1-methyl-3-(1-ethyl-1-silacyclobutyl)-cyclopentadienyl)titanium dichloride, bis(1-methyl-3-(1-propyl-1-silacyclobutyl)-cyclopentadienyl)titanium dichloride,
bis(1-methyl-3-(1-butyl-1-silacyclobutyl)-cyclopentadienyl)titanium dichloride,
bis(1-ethyl-3-(1-methyl-1-silacyclobutyl)-cyclopentadienyl)titanium dichloride,
bis(1-ethyl-3-(1-ethyl-1-silacyclobutyl)-cyclopentadienyl)titanium dichloride,
bis(1-ethyl-3-(1-propyl-1-silacyclobutyl)-cyclopentadienyl)titanium dichloride,
bis(1-(1-butyl-1-silacyclobutyl)-3-ethyl-cyclopentadienyl)titanium dichloride,
bis(1-butyl-3-(1-methyl-1-silacyclobutyl)-cyclopentadienyl)titanium dichloride,
bis(1-butyl-3-(1-ethyl-1-silacyclobutyl)-cyclopentadienyl)titanium dichloride,
bis(1-butyl-3-(1-propyl-1-silacyclobutyl)-cyclopentadienyl)titanium dichloride,
bis(1-butyl-3-(1-butyl-1-silacyclobutyl)-cyclopentadienyl)titanium dichloride,
bis(1-(1-methyl-1-silacyclobutyl)indenyl)titanium dichloride,
bis(1-(1-ethyl-1-silacyclobutyl)-indenyl)titanium dichloride,
bis(1-(1-propyl-1-silacyclobutyl)-indenyl)titanium dichloride,
bis(1-(1-butyl-1-silacyclobutyl)-indenyl)titanium dichloride,
bis(1-(1-methyl-1-silacyclobutyl)tetrahydroindenyl)titanium dichloride,
bis(1-(1-ethyl-1-silacyclobutyl) tetrahydroindenyl)titanium dichloride,
bis(1-(1-propyl-1-silacyclobutyl) tetrahydroindenyl)titanium dichloride,
bis(1-(1-butyl-1-silacyclobutyl) tetrahydroindenyl)titanium dichloride,
bis(9-(1-methyl-1-silacyclobutyl)fluorenyl)titanium dichloride,
bis(9-(1-ethyl-1-silacyclobutyl)fluorenyl)titanium dichloride,
bis(9-(1-propyl-1-silacyclobutyl)fluorenyl)titanium dichloride,
bis(9-(1-butyl-1-silacyclobutyl)fluorenyl)titanium dichloride,
(1-(1-methyl-1-silacyclobutyl)indenyl)(cyclopentadienyl)titanium dichloride,
(1-(1-ethyl-1-silacyclobutyl)indenyl)(cyclopentadienyl)titanium dichloride,
(1-(1-propyl-1-silacyclobutyl)indenyl)(cyclopentadienyl)titanium dichloride,
(1-(1-butyl-1-silacyclobutyl)indenyl)(cyclopentadienyl)titanium dichloride,
(1-(1-methyl-1-silacyclobutyl)tetrahydroindenyl)(cyclopentadienyl)titanium dichloride,
(1-(1-ethyl-1-silacyclobutyl)tetrahydroindenyl)(cyclopentadienyl)titanium dichloride,
(1-(1-propyl-1-silacyclobutyl)tetrahydroindenyl)(cyclopentadienyl)titanium dichloride,
(1-(1-butyl-1-silacyclobutyl)tetrahydroindenyl)(cyclopentadienyl)titanium dichloride,
(1-(1-methyl-1-silacyclobutyl)indenyl)(pentamethyl-cyclopentadienyl)titanium dichloride,
(1-(1-ethyl-1-silacyclobutyl)indenyl)(pentamethyl-cyclopentadienyl)titanium dichloride,
(1-(1-propyl-1-silacyclobutyl)indenyl)(pentamethyl-cyclopentadienyl)titanium dichloride,
(1-(1-butyl-1-silacyclobutyl)indenyl)(pentamethyl-cyclopentadienyl)titanium dichloride,
(1-(1-methyl-1-silacyclobutyl)pentahydroindenyl)(pentamethylcyclopentadienyl)titanium dichcoride,
(1-(1-ethyl-1-silacyclobutyl)pentahydroindenyl)(pentamethylcyclopentadienyl)titanium dichloride,
(1-(1-propyl-1-silacyclobutyl)pentahydroindenyl)(pentamethylcyclopentadienyl)titanium dichloride,
(1-(1-butyl-1-silacyclobutyl)pentahydroindenyl)(pentamethylcyclopentadienyl)titanium dichloride,
(1-(1-methyl-1-silacyclobutyl)cyclopentadienyl)(cyclopentadienyl)titanium dichloride,
(1-(1-ethyl-1-silacyclobutyl)cyclopentadienyl)(cyclopentadienyl)titanium dichloride,
(1-(1-propyl-1-silacyclobutyl)cyclopentadienyl)(cyclopentadienyl)titanium dichloride,
(1-(1-butyl-1-silacyclobutyl)cyclopentadienyl)(cyclopentadienyl)titanium dichloride,
(1-methyl-3-(1-methyl-1-silacyclobutyl)cyclopentadienyl)(cyclopentadienyl)titanium dichioride,
(1-(1-ethyl-1-silacyclobutyl)-3-methyl-cyclopentadienyl)(cyclopentadienyl)titanium dichloride,
(1-(1-propyl-1-silacyclobutyl)-3-methyl-cyclopentadienyl)(cyclopentadienyl)titanium dichloride,
(1-(1-butyl-1-silacyclobutyl)-3-methyl-cyclopentadienyl)(cyclopentadienyl)titanium dichloride,
((1-methyl-1-silacyclobutyl)cyclopentadienyl)(pentamethylcyclopentadienyl)titanium dichloride,
((1-ethyl-1-silacyclobutyl)cyclopentadienyl)(pentamethylcyclopentadienyl)titanium dichloride,
((1-propyl-1-silacyclobutyl)cyclopentadienyl)(pentamethylcyclopentadienyl)titanium dichloride,
((1-butyl-1-silacyclobutyl)cyclopentadienyl)(pentamethylcyclopentadienyl)titanium dichloride,
(1-methyl-3-(1-methyl-1-silacyclobutyl)cyclopentadienyl)(pentamethylcyclo pentadienyl) titanium dichloride,
(1-(1-ethyl-1-silacyclobutyl)-3-methyl-cyclopentadienyl)(pentamethylcyclo pentadienyl) titanium dichloride,
(1-methyl-3-(1-propyl-1-silacyclobutyl)cyclopentadienyl)(pentamethylcyclo pentadienyl) titanium dichloride,
(1-(1-butyl-1-silacyclobutyl)-3-methyl-cyclopentadienyl)(pentamethylcyclo pentadienyl) titanium dichloride,
bis(9-(1-methyl-1-silacyclobutyl)-fluorenyl) titanium dichloride,
bis(9-(1-ethyl-1-silacyclobutyl)-fluorenyl) titanium dichloride,
bis(9-(1-propyl-1-silacyclobutyl)-fluorenyl) titanium dichloride,
bis(9-(1-butyl-1-silacyclobutyl)-fluorenyl) titanium dichloride,
(9-(1-methyl-1-silacyclobutyl)-fluorenyl)(cyclopentadienyl) titanium dichloride,
(9-(1-ethyl-1-silacyclobutyl)-fluorenyl)(cyclopentadienyl) titanium dichloride,
(9-(1-propyl-1-silacyclobutyl)-fluorenyl)(cyclopentadienyl) titanium dichloride, (9-(1-butyl-1-silacyclobutyl)-fluorenyl)(cyclopentadienyl) titanium dichloride,
(9-(1-methyl-1-silacyclobutyl)-fluorenyl) (pentamethylcyclopentadienyl) titanium dichtoride,
(9-(1-ethyl-1-silacyclobutyl)-fluorenyl)(pentamethylcyclopentadienyl) titanium dichloride,
(9-(1-propyl-1-silacyclobutyl)-fluorenyl) (pentamethylcyclopentadienyl) titanium dichloride,
(9-(1-butyl-1-silacyclobutyl)-fluorenyl)(pentamethylcyclopentadienyl) titanium dichloride,
dimethylsilyl(1-(1-methyl-1-silacyclobutyl) cyclopentadienyl) (tert-butylamido)titanium dichloride,
dimethylsilyl(1-(1-methyl-1-silacyclobutyl) cyclopentadienyl)(sec-butylamido)titanium dichloride,
ethylene-bis(1-(1-methyl-1-silacyclobutyl)indenyl) titanium dichloride,
ethylene-bis(1-(1-ethyl-1-silacyclobutyl)indenyl)titanium dichloride,
ethylene-bis(1-(1-propyl-1-silacyclobutyl)indenyl) titanium dichloride,
ethylene-bis(1-(1-butyl-1-silacyclobutyl)indenyl) titanium dichloride,
ethylene-bis(1-(1-methyl-1-silacyclobutyl) tetrahydroindenyl)titanium dichioride,
ethylene-bis(1-(1-ethyl-1-silacyclobutyl) tetrahydroindenyl)titanium dichloride,
ethylene-bis(1-(1-propyl-1-silacyclobutyl) tetrahydroindenyl)titanium dichloride,
ethylene-bis(1-(1-butyl-1-silacyclobutyl) tetrahydroindenyl)titanium dichloride,
2,2-propyl-bis(3-(1-methyl-1-silacyclobutyl)-1-indenyl) titanium dichloride,
2,2-propyl-bis(3-(1-ethyl-1-silacyclobutyl)-1-indenyl) titanium dichloride,
2,2-propyl-bis(3-(1-butyl-1-silacyclobutyl)-1-indenyl) titanium dichloride,
2,2-propyl-bis(3-(1-methyl-1-silacyclobutyl)-1-tetrahydroindenyl)titanium dichloride,
2,2-propyl-bis(3-(1-ethyl-1-silacyclobutyl)-1-tetrahydroindenyl)titanium dichloride,
2,2-propyl-bis(3-(1-butyl-1-silacyclobutyl)-1-tetrahydroindenyl)titanium dichloride,
ethylene-bis(3-(1-methyl-1-silacyclobutyl) cyclopentadienyl)titanium dichloride,
2,2-propyl-bis(3-(1-methyl-1-silacyclobutyl) cyclopentadienyl)titanium dichloride,
2,2-propyl-(3-(1-methyl-1-silacyclobutyl) cyclopentadienyl)(cyclopentadienyl)titanium dichloride,
2,2-propyl-(3-(1-methyl-1-silacyclobutyl) cyclopentadienyl)(pentamethyl cyclopentadienyl)titanium dichloride.

The typical and non-limiting examples of the metallocene compounds of the formula 1 or 2, in the case where the transition metal is hafnium, include
bis((1-methyl-1-silacyclobutyl)-cyclopentadienyl) hafnium dichloride,
bis((1-ethyl-1-silacyclobutyl)-cyclopentadienyl)hafnium dichloride,
bis((1-propyl-1-silacyclobutyl)-cyclopentadienyl) hafnium dichloride,
bis((1-butyl-1-silacyclobutyl)-cyclopentadienyl)hafnium dichloride,
bis(1-methyl-3-(1-methyl-1-silacyclobutyl)-cyclopentadienyl)hafnium dichloride,
bis(1-methyl-3-(1-ethyl-1-silacyclobutyl)-cyclopentadienyl)hafnium dichloride,
bis(1-methyl-3-(1-propyl-1-silacyclobutyl)-cyclopentadienyl)hafnium dichloride,
bis(1-methyl-3-(1-butyl-1-silacyclobutyl)-cyclopentadienyl)hafnium dichloride,
bis(1-ethyl-3-(1-methyl-1-silacyclobutyl)-cyclopentadienyl) hafnium dichloride,
bis(1-ethyl-3-(1-ethyl-1-silacyclobutyl)-cyclopentadienyl)hafnium dichloride,
bis(1-ethyl-3-(1-propyl-1-silacyclobutyl)-cyclopentadienyl)hafnium dichloride,
bis(1-(1-butyl-1-silacyclobutyl)-3-ethyl-cyclopentadienyl)hafnium dichloride,
bis(1-butyl-3-(1-methyl-1-silacyclobutyl)-cyclopentadienyl)hafnium dichloride,
bis(1-butyl-3-(1-ethyl-1-silacyclobutyl)-cyclopentadienyl)hafnium dichloride,
bis(1-butyl-3-(1-propyl-1-silacyclobutyl)-cyclopentadienyl)hafnium dichloride,
bis(1-butyl-3-(1-butyl-1-silacyclobutyl)-cyclopentadienyl)hafnium dichloride,
bis(1-(1-methyl-1-silacyclobutyl)indenyl)hafnium dichloride,
bis(1-(1-ethyl-1-silacyclobutyl)indenyl)hafnium dichloride,
bis(1-(1-propyl-1-silacyclobutyl)indenyl)hafnium dichloride,
bis(1-(1-butyl-1-silacyclobutyl)indenyl)hafnium dichloride,
bis(1-(1-methyl-1-silacyclobutyl)tetrahydroindenyl) hafnium dichloride,
bis(1-(1-ethyl-1-silacyclobutyl) tetrahydroindenyl) hafnium dichloride,
bis(1-(1-propyl-1-silacyclobutyl) tetrahydroindenyl) hafnium dichloride,
bis(1-(1-butyl-1-silacyclobutyl) tetrahydroindenyl) hafnium dichloride,
bis(9-(1-methyl-1-silacyclobutyl)fluorenyl)hafnium dichloride,
bis(9-(1-ethyl-1-silacyclobutyl)fluorenyl)hafnium dichloride,
bis(9-(1-propyl-1-silacyclobutyl)fluorenyl) hafnium dichloride,
bis(9-(1-butyl-1-silacyclobutyl)fluorenyl)hafnium dichloride,
(1-(1-methyl-1-silacyclobutyl)indenyl)(cyclopentadienyl)hafnium dichloride,
(1-(1-ethyl-1-silacyclobutyl)indenyl)(cyclopentadienyl) hafnium dichloride,
(1-(1-propyl-1-silacyclobutyl)indenyl)(cyclopentadienyl) hafnium dichloride,
(1-(1-butyl-1-silacyclobutyl)indenyl)(cyclopentadienyl) hafnium dichloride,
(1-(1-methyl-1-silacyclobutyl)tetrahydlroinden yl) (cyclopentadienyl)hafnium dichloride,
(1-(1-ethyl-1-silacyclobutyl)tetrahydroindenyl) (cyclopentadienyl)hafnium dichloride,
(1-(1-propyl-1-silacyclobutyl)tetrahydroindenyl) (cyclopentadienyl)hafnium dichloride, (1-(1-butyl-1-silacyclobutyl)tetrahydroindenyl)(cyclopentadienyl)hafnium dichloride, (1-(1-methyl-1-silacyclobutyl)indenyl)(pentamethylcyclopentadienyl)hafnium dichloride, (1-(1-ethyl-1-silacyclobutyl)indenyl)(pentamethylcyclopentadienyl)hafnium dichloride, (1-(1-propyl-1-silacyclobutyl)indenyl)(pentamethylcyclopentadienyl)hafnium dichloride, (1-(1-butyl-1-silacyclobutyl)indenyl)(pentamethylcyclopentadienyl)hafnium dichloride, (1-(1-methyl-1-silacyclobutyl)cyclopentadienyl)(cyclopentadienyl)hafnium dichloride, (1-(1-ethyl-1-silacyclobutyl)cyclopentadienyl)(cyclopentadienyl)hafnium dichloride, (1-(1-propyl-1-silacyclobutyl)cyclopentadienyl)(cyclopentadienyl)hafnium dichloride, (1-(1-butyl-1-silacyclobutyl)cyclopentadienyl)(cyclopentadienyl)hafnium dichloride, (1-methyl-3-(1-methyl-1-silacyclobutyl)cyclopentadienyl)(cyclopentadienyl)hafnium dichloride, (1-(1-ethyl-1-silacyclobutyl)-3-methyl-cyclopentadienyl)(cyclopentadienyl)hafnium dichloride, (1-(1-propyl-1-silacyclobutyl)-3-methyl-cyclopentadienyl)(cyclopentadienyl)hafnium dichloride, (1-(1-butyl-1-silacyclobutyl)-3-methyl-cyclopentadienyl)(cyclopentadienyl)hafnium dichloride, ((1-methyl-1-silacyclobutyl)cyclopentadienyl)(pentamethylcyclopentadienyl)hafnium dichloride, ((1-ethyl-1-silacyclobutyl)cyclopentadienyl)(pentamethylcyclopentadienyl)hafnium dichloride, ((1-propyl-1-silacyclobutyl)cyclopentadienyl)(pentamethylcyclopentadienyl)hafnium dichloride, ((1-butyl-1-silacyclobutyl)cyclopentadienyl)(pentamethylcyclopentadienyl)hafnium dichloride, (1-methyl-3-(1-methyl-1-silacyclobutyl)cyclopentadienyl)(pentamethylcyclopentadienyl)hafnium dichloride, (1-(1-ethyl-1-silacyclobutyl)-3-methyl-cyclopentadienyl)(pentamethylcyclopentadienyl)hafnium dichloride, (1-methyl-3-(1-propyl-1-silacyclobutyl)cyclopentadienyl)(pentamethylcyclopentadienyl)hafnium dichloride, (1-(1-butyl-1-silacyclobutyl)-3-methyl-cyclopentadienyl)(pentamethylcyclopentadienyl)hafnium dichloride, bis(9-(1-methyl-1-silacyclobutyl)-fluorenyl)hafnium dichloride, bis(9-(1-ethyl-1-silacyclobutyl)-fluorenyl)hafnium dichloride, bis(9-(1-propyl-1-silacyclobutyl)-fluorenyl)hafnium dichloride, bis(9-(1-butyl-1-silacyclobutyl)-fluorenyl)hafnium dichloride, (9-(1-methyl-1-silacyclobutyl)-fluorenyl)(cyclopentadienyl)hafnium dichloride, (9-(1-ethyl-1-silacyclobutyl)-fluorenyl)(cyclopentadienyl)hafnium dichloride, (9-(1-propyl-1-silacyclobutyl)fluorenyl)(cyclopentadienyl)hafnium dichloride, (9-(1-butyl-1-silacyclobutyl)-fluorenyl)(cyclopentadienyl)hafnium dichloride, (9-(1-methyl-1-silacyclobutyl)-fluorenyl)(pentamethylcyclopentadienyl)hafnium dichloride, (9-(1-ethyl-1-silacyclobutyl)-fluorenyl)(pentamethylcyclopentadienyl)hafnium dichloride, (9-(1-propyl-1-silacyclobutyl)-fluorenyl)(pentamethylcyclopentadienyl)hafnium dichloride, (9-(1-butyl-1-silacyclobutyl)-fluorenyl)(pentamethylcyclopentadienyl)hafnium dichloride, dimethylsily(-1-(1-methyl-1-silacyclobutyl)cyclopentadienyl)(tert-butylamido)hafnium dichloride, dimethylsilyl(1-(1-methyl-1-silacyclobutyl)cyclopentadienyl)(sec-butylamido)hafnium dichloride, ethylene-bis(1-(1-methyl-1-silacyclobutyl)indenyl)hafnium dichloride, ethylene-bis(1-(1-ethyl-1-silacyclobutyl)indenyl)hafnium dichloride, ethylene-bis(1-(1-propyl-1-silacyclobutyl)indenyl)hafnium dichloride, ethylene-bis(1-(1-butyl-1-silacyclobutyl)indenyl)hafnium dichloride, ethylene-bis(1-(1-methyl-1-silacyclobutyl)tetrahydroindenyl)hafnium dichloride, ethylene-bis(1-(1-ethyl-1-silacyclobutyl)tetrahydroindenyl)hafnium dichloride, ethylene-bis(1-(1-propyl-1-silacyclobutyl)tetrahydroindenyl)hafnium dichloride, ethylene-bis(1-(1-butyl-1-silacyclobutyl)tetrahydroindenyl)hafnium dichloride, 2,2-propyl-bis(3-(1-methyl-1-silacyclobutyl)-1-indenyl)hafnium dichloride, 2,2-propyl-bis(3-(1-ethyl-1-silacyclobutyl)-1-indenyl)hafnium dichioride, 2,2-propyl-bis(3-(1-butyl-1-silacyclobutyl)-1-indenyl)hafnium dichloride, 2,2-propyl-bis(3-(1-methyl-1-silacyclobutyl)-1-tetrahydroindenyl)hafnium dichloride, 2,2-propyl-bis(3-(1-ethyl-1-silacyclobutyl)-1-tetrahydroindenyl)hafnium dichloride, 2,2-propyl-bis(3-(1-butyl-1-silacyclobutyl)-1-tetrahydroindenyl)hafnium dichioride, ethylene-bis(3-(1-methyl-1-silacyclobutyl)cyclopentadienyl)hafnium dichloride, 2,2-propyl-bis(3-(1-methyl-1-silacyclobutyl)cyclopentadienyl)hafnium dichioride, 2,2-propyl-(3-(1-methyl-1-silacyclobutyl)cyclopentadienyl)(cyclopentadienyl)hafnium dichloride, 2,2-propyl-(3-(1-methyl-1-silacyclobutyl)cyclopentadienyl)(pentamethyl cyclopentadienyl)hafnium dichloride.

The metallocene compounds can be used as catalysts for polymerizing olefin monomers in combination with an activator such as methylaluminoxane (MAO), modified methylaluminoxane (MMAO), aromatic boron compounds substituted with fluoride [for example, tri(butyl)ammonium tetra(pentafluorophenyl)boron, N,N-dimethylanilinium tetra(pentafluorophenyl) boron], or modified clays [for example, N,N-dimethylanilinium montmorillonite, N,N-dimethylanilinium hectorite]. If necessary, the metallocene compounds and activators can be affixed to a solid carrier to form a carrier-supported catalyst.

In the present invention, any aluminoxane and modified aluminoxane available from conventional commercial manufacturer can be used as the activator. The aluminoxane can be prepared by conventional methods such as method of adding appropriate amount of water to trialkylaluminum, method of reacting hydrated hydrocarbon compound or inorganic hydrated salt with trialkylaluminum, and the like. Generally, mixture of linear and ring type aluminoxanes is obtained by the methods. In this invention, linear or ring type oligomer of hydrocarbyl aluminoxane can be used alone or in combination. The representative example of the linear and ring type aluminoxanes are shown in the following formula 4 and 5, respectively.

[formula 4]

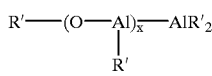

[formula 5]

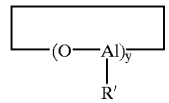

In the formula 4 and 5, R' is hydrocarbyl radical, preferably, linear or branched alkyl radical having 1 to 10 carbon atoms, more preferably, most of R' is methyl, x is an integer of 1 to 50, preferably, 10 to 40, and y is an integer of 3 to 50, preferably, 10 to 40. The aluminoxane is commercially available in the form of hydrocarbon solution. In the present invention, the preferable form of the aluminoxane is an aromatic hydrocarbon solution of the aluminoxane, and the more preferable form is a toluene solution of the aluminoxane.

In combination with the activator, the metallocene compounds of the present invention can be used as catalysts for polymerizing α-olefin having 2 to 12 carbon atoms. In polymerization reaction, the metallocene compound of the present invention can be used in the homogeneous state, in which the metallocene compound and activator are uniformly dissolved in a reactor, and in the carrier supported state, in which the metallocene compound and/or the activator are supported by an inorganic oxide carrier(e.g., silica, alumina, or silica-alumina mixture) as well as in an insoluble particle form. Therefore, the catalyst including the metallocene compound of the present invention and the activator can be applied to various polymerization methods including liquid phase, slurry phase and gas phase olefin polymerization. The polymerization catalysts may include two or more different metallocene compounds of the formula 1 or 2, and can polymerize ethylene, if necessary, in the presence of desired amounts of other kinds of olefins. Other olefins is preferably α-olefin having 3 to 10 carbon atoms, and the more preferable α-olefin include propylene, 1-butene, 1-pentene, 3-methyl-1-butene, 1-hexene, 4-methyl-1-pentene, 3-methyl-1-pentene, 1-heptene, 1-octene, 1-decene, 4,4-dimethyl-1-pentene, 4,4-diethyl-1-hexene, 3,4-dimethyl-1-hexene, and their derivatives and mixture.

The conditions of the olefin polymerization can be broadly varied according to the kinds of the olefin and metallocene compound, type of the catalyst being used in the polymerization (homogeneous form or carrier supported form), polymerization method (liquid phase, slurry phase or gas phase polymerization), degree of polymerization, and the like. Usually, the polymerization temperature is in the range of about 20 to about 200° C., and the polymerization pressure is in the range of 10 to 7000 psig. The molecular weight of polymer can be controlled by changing the polymerization temperature or injecting hydrogen into the reactor.

The amounts of the catalyst components can be also broadly varied, and the preferable mole ratio of aluminum in the aluminoxane to transition metal in the metallocene compound ([aluminum]: [transition metal]) is in the range of 1:1 to 100,000:1, more preferably, 5:1 to 15,000:1. The olefin polymerization is generally performed in the presence of liquid or gas phase diluent. The diluent should be a non-reactive material to the catalyst system for preventing adverse effect, and substances which deteriorates the catalytic activity of the metallocene compound should be removed from the diluent before the diluent is used in the olefin polymerization. Preferable diluent includes propane, butane, isobutane, pentane, hexane, heptane, octane, cyclohexane, methylcyclohexane, toluene, xylene, their derivatives and their mixture.

Preferred and non-limiting examples will be provided below in order to more fully illustrate the present invention. In the following examples, the metallocene compounds were prepared by the Schlenk method to block air and moisture, and purified and dried nitrogen was used as inert gas. The dichloromethane solvent was dehydrated with calcium hydride, and the other solvents were dehydrated with sodium under inert nitrogen atmosphere before use. Deuterated solvent for Nuclear Magnetic Resonance (NMR) Spectrometry was kept with molecular sieve and used at need.

EXAMPLE 1

Preparation of bis((1-methyl-1-silacyclobutyl)-indenyl)zirconium dichloride [(MSCB-Ind)$_2$ZrCl$_2$]

A. Preparation of 1-chloro-1-methylsilacyclobutane

After adding 20 g of magnesium powder and 500 mL of diethyl ether into a 1000 mL two-necked round flask under nitrogen atmosphere, 1 mL of 1,2-dibromoethane was added, and the solution was stirred for about 20 minutes to activate magnesium. 47.7 g of dichloro(3-chloropropyl) methylsilane (Aldrich, 98%) diluted with 100 mL diethyl ether was then added slowly with stirring for about 1 hour. This reaction mixture was refluxed for 7 days. After the mixture was cooled to room temperature, reflux condenser was removed, and volatile material was separated from solid by trap-to-trap distillation. This solution was fractional-distilled slowly to obtain 13.33 g of colorless 1-chloro-1-methylsilacyclobutane, which was obtained at the temperature of 102–105° C.

B. Preparation of 1-(1-methyl-1-silacyclobutyl)indene

After adding 5.195 g (42.55 mmol) of indenyl lithium into a flask under nitrogen atmosphere, and mounting a reflux condenser to the flask, 50 mL of hexane was added to form suspension. Then, 5.7 mL (46.53 mmol) of 1-chloro-1-methylsilacyclobytane was injected into the suspension of indenyl lithium with syringe and the inner wall of the flask was washed with 10 mL of hexane. After refluxing the reaction mixture for 24 hours, the mixture was filtered with celite. The solvent was then evaporated from the filtered reaction mixture, and which was purified through column chromatography to obtain 7.54 g (yield: 88.6%) of 1-(1-methyl-1-silacyclobutyl)indene having the following 1H NMR (CDCl$_3$, ppm) data: 7.54 (d, 2H), 7.33–7.20 (m, 2H), 7.03 (d, 1H), 6.72 (d, 1H), 3.86 (s, 1H), 2.10–2.02 (m, 2H), 1.16–1.02 (m, 4H), 0.02 (s, 1H).

C. Preparation of 1-(1-methyl-1-silacyclobutyl)indene lithium

Under nitrogen atmosphere, 7.54 g of the compound obtained in the above step B was dissolved into 50 mL of hexane. Then, 24 mL of 1.6 M butyl lithium in hexane was added dropwisely at 0° C., and then the reaction mixture was stirred at room temperature overnight. The resultant white solid was filtered, washed five times with each of 10 mL of hexane, and dried under vacuum to obtain 7.3 g (yield: 94%) of white powder.

D. Preparation of bis(1-methyl-1-silacyclobutyl)indenyl) zirconium dichloride

Under nitrogen atmosphere, 4.46 g (21.65 mmol) of lithium 1-(1-methyl-1-silacyclobutyl)indene and 4.08 g (10.81 mmol) of $ZrCl_4(THF)_2$, which was obtained by reacting $ZrCl_4$ with THF, was placed in each flask respectively. 50 mL of dichloromethane was added to each flask with stirring for about 30 minutes to form suspension. The suspension of $ZrCl_4(THF)_2$ in the second flask was slowly added into the suspension of lithium 1-(1-methyl-1-silacyclobutyl)indene in the first flask, and then the remained solid in the second flask was washed with 10 mL of dichloromethane and added into the first flask. With repeating the washing and addition process for three times, the reaction mixture was stirred overnight. After completion of reaction, LiCl was filtered and removed from yellowish solution with 11G4 filter. The solvent was then evaporated from the filtrate under vacuum until solid powder is formed in the filtrate. The condensed filtrate was placed at −20° C. for about 24 hours for crystallization. The yellowish powder formed by crystallization was filtered, washed several times with hexane, and dried under vacuum overnight to obtain 5.25 g (yield: 86.6%) of pure bis((1-methyl-1-silacyclobutyl)indenyl)zirconium dichloride having the following 1H NMR ($CDCl_3$, ppm) data: δ7.9–7.27 (m, 8H, Ar), 6.59 (d, 2H, 2-lndH), 6.35 (d, 2H, 3-lndH), 2.36–2.11 (m, 4H), 1.50–1.22 (m, 4H), 0.68 (s, 6H, 2CH3).

EXAMPLE 2

Preparation of bis((1-methyl-1-silacyclobutyl)-cyclopentadienyl)zirconium dichloride [$(MSCB-Cp)_2ZrCl_2$]

A. Preparation of cyclopentadienyl sodium

After slowly adding 70 g (1.06 mol) of cyclopentadiene into 300 mL of THF solvent including 24 g (1 mol) of sodium at −78° C., the reaction mixture was stirred at room temperature for about 30 minutes. After the completion of reaction, the produced salt was filtered, washed five times with 50 mL of hexane, and dried under vacuum for about 48 hours to obtain 80.4 g (yield: 91.3%) of powder of cyclopentadienyl sodium.

B. Preparation of bis((1-methyl-1-silacyclobutyl)-cyclopentadienyl) zirconium dichloride Under nitrogen atmosphere, 4 g (45.4 mmol) of the cyclopentadienyl sodium was placed into a flask equipped with reflux condenser, and then 100 mL of hexane was added to form suspension. To this flask was injected 5.5 mL (44.9 mmol) of 1-chloro-1-methylsilacyclobutane with syringe, and then the remained reactant on the wall of the flask was washed with 10 mL of hexane. The reaction mixture was refluxed for about 20 hours, and then the solvent was removed.

To perform the next reaction consecutively, 100 mL of diethyl ether was added, and then 23 mL of 1.6 M butyl lithium in hexane was added dropwisely at 0° C. The reaction mixture was stirred at room temperature overnight to complete the reaction. The produced white precipitate was filtered, washed five times with each 10 mL of hexane, and dried under vacuum to obtain white powder of 1-(1-methyl-1-silacyclobutyl)cyclopentadienyl lithium.

Under nitrogen atmosphere, the obtained 1-(1-methyl-1-silacyclobutyl)cyclopentadienyl lithium and 6.5 g (17.2 mmol) of $ZrCl_4(THF)_2$ was placed in each flask respectively, and 50 mL of tetrahydrofuran (THF) was added to each flask to form solution with stirring for about 30 minutes. The solution of $ZrCl_4(THF)_2$ in the second flask was slowly added into the solution of 1-(1-methyl-1-silacyclobutyl) cyclopentadienyl lithium in the first flask, and then the remained reactant in the second flask was washed with 10 mL of tetrahydrofuran and added into the first flask. After repeating the washing and addition process for three times, the reaction mixture was stirred at 25° C. for 20 hours. After completion of reaction, the solvent was removed from the bright gray solution, and then 20 mL of dichloromethane was added. At this time, slurries of LiCl was formed. The LiCl was filtered and removed with 11G4 filter. The solvent was then evaporated from the filtrate under vacuum until solid powder is formed in the filtrate. The condensed filtrate was placed at −20° C. for about 48 hours for crystallization. The white powder formed by crystallization was washed several times with hexane, and dried under vacuum overnight to obtain the pure product of 4.6 g (58% of yield based on $ZrCl_4$) of bis((1-methyl-1-silacyclobutyl)-cyclopentadienyl)zirconium dichloride having the following 1H NMR ($CDCl_3$, ppm) data: δ6.46–6.82 (m, 8H, —C5H4), 2.09–2.3 (m, 4H), 1.19–1.34 (m, 8H), 0.63 (s, 6H, —CH3).

EXAMPLE 3

Preparation of bis(1-methyl-3-(1-methyl-1-silacyclobutyl)-cyclopentadienyl)zirconium dichloride [$(MeMSCB-Cp)_2ZrCl_2$]

Under nitrogen atmosphere, 2.08 g of methylcyclopentadiene was placed into a flask. Then 50 mL tetrahydrofuran (THF) was added to the flask and cooled to −30° C., and then 16.2 mL of 1.6 M normal butyl lithium in hexane was added for about 20 minutes. The reaction mixture was further stirred at room temperature for about 1 hour, and 4.0 mL of 1-chloro-1-methylsilacyclobutane was slowly added into the flask and further stirred for about 12 hours. The solvent THF was removed from the solution and 30 mL of diethyl ether was added to it. To effectuate the next reaction, LiCl was removed from the solution by filtration.

Next, 16.2 mL of 1.6 M normal butyl lithium in hexane was added into the flask at 0° C. and further stirred at room temperature for about 2 hours. The suspension of 4.90 g (12.9 mmol) of $ZrCl_4(THF)_2$ in 50 mL of diethyl ether was slowly added for 1 hour and then further stirred for 12 hours. The reaction mixture was filtered under nitrogen atmosphere, and the solvent was evaporated from the filtrate under vacuum. To the concentrate was added 30 mL of hexane to form precipitate, which was filtered and dried under vacuum to obtain the final product of white powder of bis(1-methyl-3-(1-methyl-1-silacyclobutyl)-cyclopentadienyl)zirconium dichloride (2.1 g; 33% of yield based on $ZrCl_4$) having the following 1H NMR ($CDCl_3$, ppm) data: δ6.60 (d, 4H), 6.03 (t, 2H), 2.29 (s, 6H), 2.27–2.06 (m, 4H), 1.32–1.16 (m, 8H), 0.58 (s, 6H).

EXAMPLE 4

Preparation of ((1-methyl-1-silacyclobutyl)indenyl) (cyclopentadienyl) zirconium dichloride [$(Cp)(MSCB-lnd)ZrCl_2$]

5 g (19.03 mmol) of cyclopentadienylzirconium trichloride ($CpZrCl_3$) was placed into a flask with 20 mL of dichloromethane to form suspension. 3.92 g (19.03 mmol) of lithium 1-(1-methyl-1-silacyclobutyl)indene was also placed into another flask with 20 mL of dichloromethane to form suspension. The suspension of $CpZrCl_3$ in the first flask was slowly added into the suspension of lithium 1-(1-methyl-1-silacyclobutyl)indene in the second flask, and then the remained reactant in the first flask was washed with 10 mL of dichloromethane and added into the second flask. After repeating the washing and addition process for three times, the reaction mixture was stirred overnight. After the completion of reaction, LiCl was filtered and removed from the formed yellowish solution with 11G4 filter. The solvent was then evaporated from the filtrate under vacuum and the remaining volatile material was also removed under vacuum at 50° C. overnight. The concentrate was then sublimated at 130° C. in the presence of 50μ Hg to obtain 5.85 g (72% of yield) of pure ((1-methyl-1-silacyclobutyl)-indenyl) (cyclopentadienyl)zirconium dichloride having the following 1H NMR (CDCl$_3$, ppm) data: δ7.95 (d, 1H), 7.92 (d, 1H), 7.42–7.28 (m, 2H), 7.14 (d, 1H), 6.84 (d, 1H), 6.10 (s, 5H, C5H5), 2.38–2.15 (m, 2H), 1.57–1.27 (m, 4H), 0.74 (s, 3H).

EXAMPLE 5

Preparation of ((1-methyl-1-silacyclobutyl)-indenyl) (pentamethylcyclopentadienyl)zirconium dichloride [(*Cp) (MSCB-Ind)ZrCl$_2$]

4.227 g (12.7 mmol) of pentamethylcyclopentadienylzirconium trichloride (*CpZrCl$_3$) was placed with 20 mL of dichloromethane into a flask to form slurry. Under nitrogen atmosphere, 2.62 g (12.7 mmol) of lithium 1-(1-methyl-1-silacyclobutyl)indene was also placed with 20 mL of dichloromethane into another flask to form suspension, and the suspension of pentamethylcyclopentadienylzirconium trichloride was slowly added to the suspension of lithium 1-(1-methyl-1-silacyclobutyl)indene. At this time, the remained *CpZrCl$_3$ on the wall of the flask was washed with 10 mL of dichloromethane and added, which was repeated three times. After the reaction mixture was stirred overnight, lithium chloride was filtered out with 11G4 filter from the produced yellowish solution. The solvent was also evaporated under vacuum to form yellowish solid, which was again sublimated at 140° C. in the presence of 50μ Hg to obtain 1.85 g (29% of yield) of ((1-methyl-1-silacyclobutyl)-indenyl) (pentamethylcyclopentadienyl)zirconium dichloride having the 1H NMR (CDCl$_3$, ppm) data: 1H-NMR (CDCl3, ppm) data: δ7.92 (d, 1H), 7.48 (d, 1H), 7.32–7.27 (m, 2H), 6.43 (d, 1H), 6.33 (d, 1H), 2.27–2.02 (m, 2H), 1.99 (s, 15H), 1.49–1.20 (m, 4H), 0.70 (s, 3H).

EXAMPLE 6

Polymerization into polyethylene

In a Glove box, the metallocene of bis((1-methyl-1-silacyclobutyl)-indenyl)zirconium dichloride [(MSCB-Ind)$_2$ZrCl$_2$] (10 mg; 0.0178 mmol) was placed into a flask. Methylaluminoxane (MAO) solution (available from Albemarle Co.; 10 wt % of MAO in toluene) was added into the flask such that the mole ratio of Al/Zr was 2,500, and then stirred for about 1 hour to form catalyst solution.

Stainless autoclave reactor (1 L) was washed one time with propane and five times with ethylene at about 85° C. to remove contaminants in the reactor, and then cooled to room temperature. The reactor was equipped with jacket for providing cooling water from outside in order to control the polymerization temperature. 200 mL of dried toluene and 0.5 mmol of triisobutylaluminum (TIBAL) as a contaminant removing agent were injected into the reactor at room temperature and then the temperature was elevated to 70° C. The prepared catalyst solution was then added into the reactor, and ethylene of 10 psig pressure was added until the pressure of the reactor increased up to 14 psig, which was the reaction pressure. After polymerization proceeded for about 1 hour, gas in the reactor was discharged and the reactor was cooled to complete the polymerization. 5% hydrochloride (HCl) solution in 300 mL of methanol was added into the polymerization product, and the product was stirred for about 2 hours to neutralize the MAO and active catalyst ingredients remained in the product. The slurry including polymer was filtered, washed with 2 L of water to remove hydrochloride, and dried at 60° C. to obtain 23 g of polymer. The yield, activity of catalyst, average molecular weight of polymer and distribution of molecular weight of polymer are shown in the following Table 1.

EXAMPLE 7

Polymerization into Polyethylene

Except that 10 mg (0.0217 mmol) of bis((1-methyl-1-silacyclobutyl)-cyclopentadienyl)zirconium dichloride [(MSCB-Cp)$_2$ZrCl$_2$], which was obtained in example 2, was used, and methylaluminoxane was used so that the molar ratio of Al/Zr was 2,780, the preparation of catalyst solution and polymerization were performed according to example 6. 26.6 g of polymer were obtained, and the yield, activity of catalyst, average molecular weight of polymer and distribution of molecular weight of polymer are shown in the following Table 1.

EXAMPLE 8

Polymerization into Polyethylene

Except that 10 mg (0.0205 mmol) of bis(1-methyl-3-(1-methyl-1-silacyclobutyl)-cyclopentadienyl)zirconium dichloride [(MeMSCB-Cp)$_2$ZrCl$_2$], which was obtained in example 3, was used, and methylaluminoxane was used so that the molar ratio of Al/Zr was 2,780, the preparation of catalyst solution and polymerization were performed according to example 6. 30.0 g of polymer were obtained, and the yield, activity of catalyst, average molecular weight of polymer and distribution of molecular weight of polymer are shown in the following Table 1.

EXAMPLE 9

Polymerization into Polyethylene

Except that 10 mg (0.0234 mmol) of ((1-methyl-1-silacyclobutyl)-indenyl)(cyclopentadienyl)zirconium dichloride [(Cp)(MSCB-Ind)ZrCl$_2$], which was obtain in example 4, was used, and methylaluminoxane was used so that the molar ratio of Al/Zr was 2,500, the preparation of catalyst solution and polymerization were performed according to example 6. 50.0 g of polymer were obtained, and the yield, activity of catalyst, average molecular weight of polymer and distribution of molecular weight of polymer are shown in the following Table 1.

EXAMPLE 10

Polymerization into Polyethylene

Except that 10 mg (0.0201 mmol) of ((1-methyl-1-silacyclobutyl)-indenyl)(pentamethylcyclopentadienyl) zirconium dichloride [(*Cp) (MSCB-Ind) ZrCl$_2$], which was obtained in example 5, was used, and methylaluminoxane was used so that the molar ratio of Al/Zr was 2,500, the preparation of catalyst solution and polymerization were performed according to example 6. 32.0 g of polymer were obtained, and the yield, activity of catalyst, average molecular weight of polymer and distribution of molecular weight of polymer are shown in the following Table 1.

COMPARATIVE EXAMPLE 1

Polymerization into Polyethylene

Except that 10 mg (0.0388 mmol) of bis(cyclopentadienyl)zirconium dichloride [(Cp)$_2$ZrCl$_2$], which is a conventional metallocene compound, was used, and methylaluminoxane was used so that the molar ratio of Al/Zr was 2,530, the preparation of catalyst solution and polymerization were performed according to example 6. 38.2 g of polymer were obtained, and the yield, activity of catalyst, average molecular weight of polymer and distribution of molecular weight of polymer are shown in the following Table 1.

COMPARATIVE EXAMPLE 2

Polymerization into Polyethylene

Except that 10 mg (0.0255 mmol) of bis(indenyl)zirconium dichloride [(Ind)$_2$ZrCl$_2$], which is a conventional metallocene compound, was used, and methylaluminoxane was used so that the molar ratio of Al/Zr was 2,550, the preparation of catalyst solution and polymerization were performed according to example 6. 30.4 g of polymer were obtained, and the yield, activity of catalyst, average molecular weight of polymer and distribution of molecular weight of polymer are shown in the following Table 1.

TABLE 1

| Example | Catalyst System | Molar Ratio of Al/Zr | Yield (g) | Activity$^a$ (Activity$^b$) | Mw | (Mw/Mn) |
|---|---|---|---|---|---|---|
| 6 | (MSCB-Ind)$_2$ZrCl$_2$ | 2,500 | 23 | 14.1 (1,290) | 58,000 | 4.1 |
| 7 | (MSCB-Cp)$_2$ZrCl$_2$ | 2,780 | 26.6 | 13.5 (1,229) | 49,000 | 4.3 |
| 8 | (MeMSCB-Cp)$_2$ZrCl$_2$ | 2,500 | 30 | 16.1 (1,466) | 129,000 | 4.6 |
| 9 | (Cp)(MSCB-Ind)ZrCl$_2$ | 2,500 | 50 | 23.4 (2,132) | 91,000 | 4.1 |
| 10 | (*Cp)(MSCB-Ind)ZrCl$_2$ | 2,500 | 32 | 17.4 (1,589) | 58,000 | 4.8 |
| Comparative Ex. 1 | (Cp)$_2$ZrCl$_2$ | 2,530 | 38.2 | 12.2 (1,116) | 26,000 | 2.8 |
| Comparative Ex. 2 | (Ind)$_2$ZrCl$_2$2 | 2,550 | 30.4 | 13.0 (1,188) | 54,000 | 4.8 |

In table 1, (Mw/Mn) represent "Distribution of Molecular Weight", and the units of Activity$^a$ and Activity$^b$ are kgPE/gZr.hour and kgPE/molZr.hour, respectively at 10 psig ethylene, 70° C., and Mw is g/mol.

As shown in the table 1, the catalyst systems of metallocene compounds including cyclopentadienyl type ligands having silacycloalkyl substituents shows similar or more excellent activities (particularly, in example 9) than the catalyst system including prior metallocene compound. Although some catalyst systems of the present invention are similar in activity to those of the prior art, polymer with higher average molecular weight can be obtained by the catalyst systems of the present invention. Thus, by using the molecular weight controlling agent (e.g., Hydrogen), polymer having desired molecular weight can be easily and commercially produced. In addition, polyolefin with various physical properties can be prepared by changing the kind and structure of the cyclopentdienyl radical substituted with silacycloalkyl group.

While the present invention has been described with respect to certain preferred embodiments and examples only, other modifications and variations may be made without departing from the spirit and scope of the present invention as set forth in the following claims.

What is claimed is:

1. A metallocene compound represented by the following formula 1 or 2, $$(CpR^1_a R^s_b)(Cp'R^2_{a'} R^s_{b'})MX_2 \qquad \text{(Formula 1)}$$

[Formula 2]

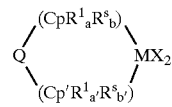

wherein, Cp and Cp', which can be the same or different, represent a radical selected from the group consisting of cyclopentadienyl radical, indenyl radical, 4,5,6,7-tetrahydro-1-indenyl radical and fluorenyl radical;

$R^1$ and $R^2$, which can be the same or different, represent phosphine, amino, alkyl having 1 to 20 carbon atoms, alkoxy, alkylamino, dialkylamino, alkoxy-alkyl, aryl, aryloxy-alkyl, alkenyl, alkylaryl or arylalkyl radical;

$R^s$ represents 1-alkyl-1-silacyclohydrocarbyl radical of the following formula 3,

[Formula 3]

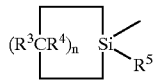

wherein, $R^3$ and $R^4$, which can be the same or different, represent hydrogen or alkyl radical having 1 to 5 carbon atoms, $R^5$ is alkyl radical having 1 to 8 carbon atoms, and n is an integer of 4 to 8;

Cp'$R^2_a R^s_{b'}$ in formula 2 can be displaced with divalent NR" radical, wherein R" represents $R^s$, alkyl radical having 1 to 12 carbon atoms, or aryl radical having 6 to 10 carbon atoms;

M represents a Group 4B, 5B, or 6B transition metal;

X, which can be the same or different, represents one radical selected from the group consisting of halogen, alkyl radical having 1 to 20 carbon atoms, aryl, alkenyl, alkylaryl, arylalkyl, alkoxy and aryloxy radicals;

Q represents alkylene radical having 1 to 4 carbon atoms, dialkyl germanium or silicon, alkyl phosphine or amine radical, bis-dialkylsilyl or bis-dialkylgermanyl having hydrocarbyl radical of 1 to 4 carbon atoms;

in formula 1, a is an integer of 0 to 4, a' is an integer of 0 to 5, b is an integer of 1 to 3, and b' is an integer of 0 to 3, wherein $1 \leq a+b \leq 5$, $0 \leq a'+b' \leq 5$; and in formula 2, a is an integer of 0 to 3, a' is an integer of 0 to 4, b is an integer of 1 to 2, and b' is an integer of 0 to 3, wherein $1 \leq a+b \leq 4$, $0 \leq a'+b' \leq 4$.

2. The metallocene compound according to claim 1, wherein M is a transition metal selected from the group consisting of titanium, zirconium and hafnium, and X is chloride.

3. A metallocene catalyst comprising:
at least one metallocene compound selected from the compounds represented by the following formula 1 or 2; and
at least one activator selected from the group consisting of aluminoxanes represented b the following formula 4 or 5, aromatic boron compounds substituted with fluoride, and modified clay;

$$(CpR^1_aR^s_b)(Cp'R^2_{a'}R^s_{b'})MX_2 \quad \text{(Formula 1)}$$

[Formula 2]

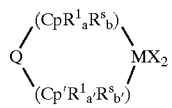

wherein, Cp and Cp', which can be the same or different, represent a radical selected from the group consisting of cyclopentadienyl radical, indenyl radical, 4,5,6,7-tetrahydro-1-indenyl radical and fluorenyl radical;

$R^1$ and $R^2$, which can be the same or different, represent phosphine, amino, alkyl having 1 to 20 carbon atoms, alkoxy, alkylamino, dialkylamino, alkoxy-alkyl, aryl, aryloxy-alkyl, alkenyl, alkylaryl or arylalkyl radical;

$R^s$ represents 1-alkyl-1-silacyclohydrocarbyl radical of the following formula 3,

[Formula 3]

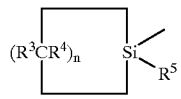

wherein, $R^3$ and $R^4$, which can be the same or different, represent hydrogen or alkyl radical having 1 to 5 carbon atoms, $R^5$ is alkyl radical having 1 to 8 carbon atoms, and n is an integer of 4 to 8;

$Cp'R^2_aR^s_{b'}$ in formula 2 can be displaced with divalent NR" radical, wherein R" represents $R^s$, alkyl radical having 1 to 12 carbon atoms, or aryl radical having 6 to 10 carbon atoms;

M represents a Group 4B, 5B, or 6B transition metal;

X, which can be the same or different, represents one radical selected from the group consisting of halogen, alkyl radical having 1 to 20 carbon atoms, aryl, alkenyl, alkylaryl, arylalkyl, alkoxy and aryloxy radicals;

Q represents alkylene radical having 1 to 4 carbon atoms, dialkyl germanium or silicon, alkyl phosphine or amine radical, bis-dialkylsilyl or bis-dialkylgermanyl having hydrocarbyl radical of 1 to 4 carbon atoms;

in formula 1, a is an integer of 0 to 4, a' is an integer of 0 to 5, b is an integer of 1 to 3, and b' is an integer of 0 to 3, wherein $1 \leq a+b \leq 5$, $0 \leq a'+b' \leq 5$;

in formula 2, a is an integer of 0 to 3, a' is an integer of 0 to 4, b is an integer of 1 to 2, and b' is an integer of 0 to 3, wherein $1 \leq a+b \leq 4$, $0 \leq a'+b' \leq 4$; and

[Formula 4]

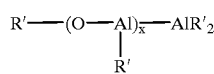

[Formula 5]

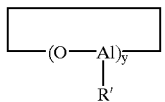

wherein, R', which can be the same or different, represent hydrocarbyl radical having 1 to 10 carbon atoms, x is an integer of 1 to 50, and y is an integer of 3 to 50.

4. The metallocene catalyst according to claim 3, wherein M is a transition metal selected from the group consisting of titanium, zirconium and hafnium, and X is chloride.

5. The metallocene catalyst according to claim 3, wherein the aromatic boron compounds substituted with fluoride is tri(butyl)ammonium tetra(pentafluorophenyl)boron or N,N-dimethylanilinium tetra(pentafluorophenyl) boron.

6. The metallocene catalyst according to claim 3, wherein the modified clay is N,N-dimethylanilinium montmorillonite or N,N-dimethylanilinium hectorite.

7. A method of polymerizing olefin with metallocene catalyst comprising:
at least one metallocene compound selected from the compounds represented by the following formula 1 or 2; and
at least one activator selected from the group consisting of aluminoxanes represented by the following formula 4 or 5, aromatic boron compounds substituted with fluoride, and modified clay;

$$(CpR^1_aR^s_b)(Cp'R^2_{a'}R^2_{b'})MX_2 \quad \text{(Formula 1)}$$

[Formula 2]

wherein, Cp and Cp', which can be the same or different, represent a radical selected from the group consisting of cyclopentadienyl radical, indenyl radical, 4,5,6,7-tetrahydro-1-indenyl radical and fluorenyl radical;

$R^1$ and $R^2$, which can be the same or different, represent phosphine, amino, alkyl having 1 to 20 carbon atoms, alkoxy, alkylamino, dialkylamino, alkoxy-alkyl, aryl, aryloxy-alkyl, alkenyl, alkylaryl or arylalkyl radical;

$R^s$ represents 1-alkyl-1-silacyclohydrocarbyl radical of the following formula 3,

[Formula 3]

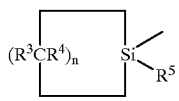

wherein, $R^3$ and $R^4$, which can be the same or different, represent hydrogen or alkyl radical having 1 to 5 carbon atoms, $R^5$ is alkyl radical having 1 to 8 carbon atoms, and n is an integer of 4 to 8;

$Cp'R^2_aR^s_{b'}$ in formula 2 can be displaced with divalent NR" radical, wherein R" represents $R^s$, alkyl radical having 1 to 12 carbon atoms, or aryl radical having 6 to 10 carbon atoms;

M represents a Group 4B, 5B, or 6B transition metal;

X, which can be the same or different, represents one radical selected from the group consisting of halogen, alkyl radical having 1 to 20 carbon atoms, aryl, alkenyl, alkylaryl, arylalkyl, alkoxy and aryloxy radicals;

Q represents alkylene radical having 1 to 4 carbon atoms, dialkyl germanium or silicon, alkyl phosphine or amine radical, bis-dialkylsilyl or bis-dialkylgermanyl having hydrocarbyl radical of 1 to 4 carbon atoms;

in formula 1, a is an integer of 0 to 4, a' is an integer of 0 to 5, b is an integer of 1 to 3, and b' is an integer of 0 to 3, wherein $1 \leq a+b \leq 5$, $0 \leq a'+b' \leq 5$;

in formula 2, a is an integer of 0 to 3, a' is an integer of 0 to 4, b is an integer of 1 to 2, and b' is an integer of 0 to 3, wherein $1 \leq a+b \leq 4$, $0 \leq a'+b' \leq 4$; and

[Formula 4]

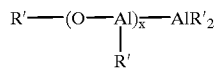

[Formula 5]

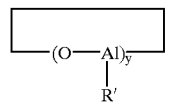

wherein, R', which can be the same or different, represent hydrocarbyl radical having 1 to 10 carbon atoms, x is an integer of 1 to 50, and y is an integer of 3 to 50.

8. The method of polymerizing olefin according to claim 7, wherein M is a transition metal selected from the group consisting of titanium, zirconium and hafnium, and X is chloride.

9. The method of polymerizing olefin according to claim 7, wherein the aromatic boron compounds substituted with fluoride is tri(butyl)ammonium tetra(pentafluorophenyl) boron or N,N-dimethylanilinium tetra(pentafluorophenyl) boron.

10. The method of polymerizing olefin according to claim 7, wherein the olefin is ethylene and/or α-olefin having 3 to 10 carbon atoms.

11. The method of polymerizing olefin according to claim 7, wherein the olefin is ethylene.

12. The method of polymerizing olefin according to claim 7, wherein the polymerizing is performed by one manner selected from the group consisting of liquid phase polymerization, slurry phase polymerization and gas phase polymerization.

\* \* \* \* \*